(12) United States Patent
Kuriyama

(10) Patent No.: US 11,141,050 B2
(45) Date of Patent: Oct. 12, 2021

(54) AUTOFOCUS CONTROL DEVICE, ENDOSCOPE APPARATUS, AND OPERATION METHOD OF AUTOFOCUS CONTROL DEVICE

(71) Applicant: OLYMPUS CORPORATION, Tokyo (JP)

(72) Inventor: Naoya Kuriyama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 133 days.

(21) Appl. No.: 16/430,960

(22) Filed: Jun. 4, 2019

(65) Prior Publication Data
US 2019/0298157 A1 Oct. 3, 2019

Related U.S. Application Data

(63) Continuation of application No. PCT/JP2016/087926, filed on Dec. 20, 2016.

(51) Int. Cl.
*A61B 1/00* (2006.01)
*A61B 1/045* (2006.01)
(Continued)

(52) U.S. Cl.
CPC ........... *A61B 1/00188* (2013.01); *A61B 1/00* (2013.01); *A61B 1/045* (2013.01);
(Continued)

(58) Field of Classification Search
CPC ....... A61B 1/00188; A61B 1/00; A61B 1/045; A61B 1/00004; A61B 1/00009;
(Continued)

(56) References Cited

U.S. PATENT DOCUMENTS

2014/0147044 A1* 5/2014 Takada ............... G09G 5/393
382/173
2015/0334289 A1* 11/2015 Yoshino ............ A61B 1/00009
348/353

(Continued)

FOREIGN PATENT DOCUMENTS

JP 2015-118337 A 6/2015
WO 2016/088186 A1 6/2016
(Continued)

OTHER PUBLICATIONS

International Search Report dated Feb. 28, 2017 received in PCT/JP2016/087926.

*Primary Examiner* — Lin Ye
*Assistant Examiner* — Tuan H Le
(74) *Attorney, Agent, or Firm* — Scully, Scott, Murphy & Presser, P.C.

(57) ABSTRACT

An autofocus control device includes a processor. The processor performs an image acquisition process of acquiring an object image captured by an imaging section, a treatment determination process of determining whether or not treatment is being performed based on the object image, a focus evaluation area setting process of setting either a preset area or a treatment area set based on the object image, as a focus evaluation area in the object image based on a determination result of the treatment determination process, and a focus control process of performing focus control of the imaging section based on a focus evaluation value of the focus evaluation area.

17 Claims, 8 Drawing Sheets

(51) Int. Cl.
  *G02B 23/24* (2006.01)
  *H04N 5/232* (2006.01)
  *H04N 5/225* (2006.01)

(52) U.S. Cl.
  CPC ..... *G02B 23/2423* (2013.01); *H04N 5/23212* (2013.01); *A61B 1/00004* (2013.01); *H04N 2005/2255* (2013.01)

(58) Field of Classification Search
  CPC .. G02B 23/2423; G02B 23/2446; G02B 7/36; G02B 23/2453; G02B 23/2469; H04N 5/23212; H04N 2005/2255; H04N 5/232127; G03B 5/00; G03B 2205/00; G03B 13/00; G03B 13/32; G03B 13/34; G03B 13/36
  See application file for complete search history.

(56) References Cited

U.S. PATENT DOCUMENTS

| | | | |
|---|---|---|---|
| 2016/0234427 A1* | 8/2016 | Yoshino | H04N 5/23212 |
| 2016/0324398 A1* | 11/2016 | Sasaki | A61B 1/00188 |
| 2017/0265725 A1 | 9/2017 | Ichikawa et al. | |
| 2017/0265726 A1 | 9/2017 | Mikami et al. | |
| 2017/0319051 A1 | 11/2017 | Kuriyama | |
| 2018/0103829 A1 | 4/2018 | Kuriyama | |

FOREIGN PATENT DOCUMENTS

| | | |
|---|---|---|
| WO | 2016/088187 A1 | 6/2016 |
| WO | 2016/117107 A1 | 7/2016 |
| WO | 2016/199264 A1 | 12/2016 |

* cited by examiner

FOCUS EVALUATION AREA
WHEN TREATMENT IS NOT BEING
PERFORMED (PRESET AREA)

AUTOFOCUS CONTROL DEVICE, ENDOSCOPE APPARATUS, AND OPERATION METHOD OF AUTOFOCUS CONTROL DEVICE

CROSS REFERENCE TO RELATED APPLICATION

This application is a continuation of International Patent Application No. PCT/JP2016/087926, having an international filing date of Dec. 20, 2016, which designated the United States, the entirety of which is incorporated herein by reference.

BACKGROUND

It is recommended that treatment be operated with an organ to be treated framed in the center of a screen in laparoscopic surgery using a surgical endoscope. However, the number of pixels of the endoscope has been getting larger in recent years and a depth of field of focus tends to be shallower, which may cause distance distribution in a center area of the screen to be deeper than the depth of field in the laparoscopic surgery. Accordingly, if a user tries to focus on the center area of the screen entirely, there may be an out-of-focus area in part.

Japanese Unexamined Patent Application Publication No. 2015-118337 has disclosed autofocus technology of an imaging device in which movement of an object is detected and when the movement is detected, a position of the object is estimated so as to move a position of a focus lens.

SUMMARY

According to one aspect of the invention, there is provided an autofocus control device comprising a processor, the processor being configured to implement:

an image acquisition process of acquiring an object image captured by an imaging section;

a treatment determination process of determining whether or not treatment is being performed based on the object image;

a focus evaluation area setting process of setting either a preset area or a treatment area set based on the object image, as a focus evaluation area in the object image based on a determination result of the treatment determination process; and a focus control process of performing focus control of the imaging section based on a focus evaluation value of the focus evaluation area.

According to another aspect of the invention, there is provided an autofocus control device comprising a processor, the processor comprising:

an image acquisition process of acquiring an object image captured by an imaging section;

a focus evaluation area setting process of detecting a treatment area in the object image based on the object image and setting the treatment area thus detected as a focus evaluation area; and a focus control process of performing focus control of the imaging section based on a focus evaluation value of the focus evaluation area.

According to another aspect of the invention, there is provided an operation method of an autofocus control device, the method comprising:

determining whether or not treatment is being performed based on an object image captured by an imaging section;

setting either a preset area or a treatment area set based on the object image, as a focus evaluation area in the object image based on a determination result of whether or not the treatment is being performed; and performing focus control of the imaging section based on a focus evaluation value of the focus evaluation area.

According to another aspect of the invention, there is provided an operation method of an autofocus control device, the method comprising:

detecting a treatment area in an object image based on an object image captured by an imaging section;

setting the treatment area thus detected as a focus evaluation area; and performing focus control of the imaging section based on a focus evaluation value of the focus evaluation area.

DESCRIPTION OF EXEMPLARY EMBODIMENTS

Exemplary embodiments are described below. Note that the following exemplary embodiments do not in any way limit the scope of the content defined by the claims laid out herein. Note also that all of the elements described in the present embodiments should not necessarily be taken as essential elements. An adoption of an autofocus control device for a surgical endoscope apparatus is described below as an example. However, the autofocus control device of the present disclosure is not limited to this, and can be applied to various imaging devices (such as endoscope apparatuses for digestive organs and for industrial use, a microscope, a digital video camera, and a digital still camera). In addition, configurations and operation of the autofocus control device are described below, however, the present disclosure may be implemented as an operation method of the autofocus control device (how the autofocus control device operates, or focus control method).

1. Configuration

When an autofocus process (hereinafter referred to as AF) is introduced into a surgical endoscope, a focus evaluation area may be set in the center of a screen to perform the AF. However, distance distribution in a center area of the screen may be deeper than a depth of field in the laparoscopic surgery, and if a user tries to focus on the center area of the screen entirely, an out-of-focus area may partially appear. Especially during treatment, if the user continues the treatment while an organ to be treated is partially out-of-focus, operation may become difficult.

Suppose that the aforementioned Japanese Unexamined Patent Application Publication No. 2015-118337 is adopted in order to solve such a problem. According to the Japanese Unexamined Patent Application Publication No. 2015-118337, if movement of an object is detected, a position of an object is estimated and a position of a focus lens is moved. Therefore, whenever the movement is detected, the organ to be treated becomes a target of the AF. As a result, even if the user desires to focus on a surgical field in the center of the screen entirely, it is impossible to focus on the entire surgical field in the center of the screen with good balance.

Therefore, in this embodiment, a treatment area is detected and the AF for focusing on the treatment area is performed. In addition, when the treatment is not being performed, the AF for focusing on the center of the screen (preset area) is performed, and when the treatment is being performed, the AF for focusing on the organ to be treated (treatment area) is performed. That is, a target of the AF is changed depending on whether or not the treatment is being performed. This embodiment is hereinafter described.

Figure 1:
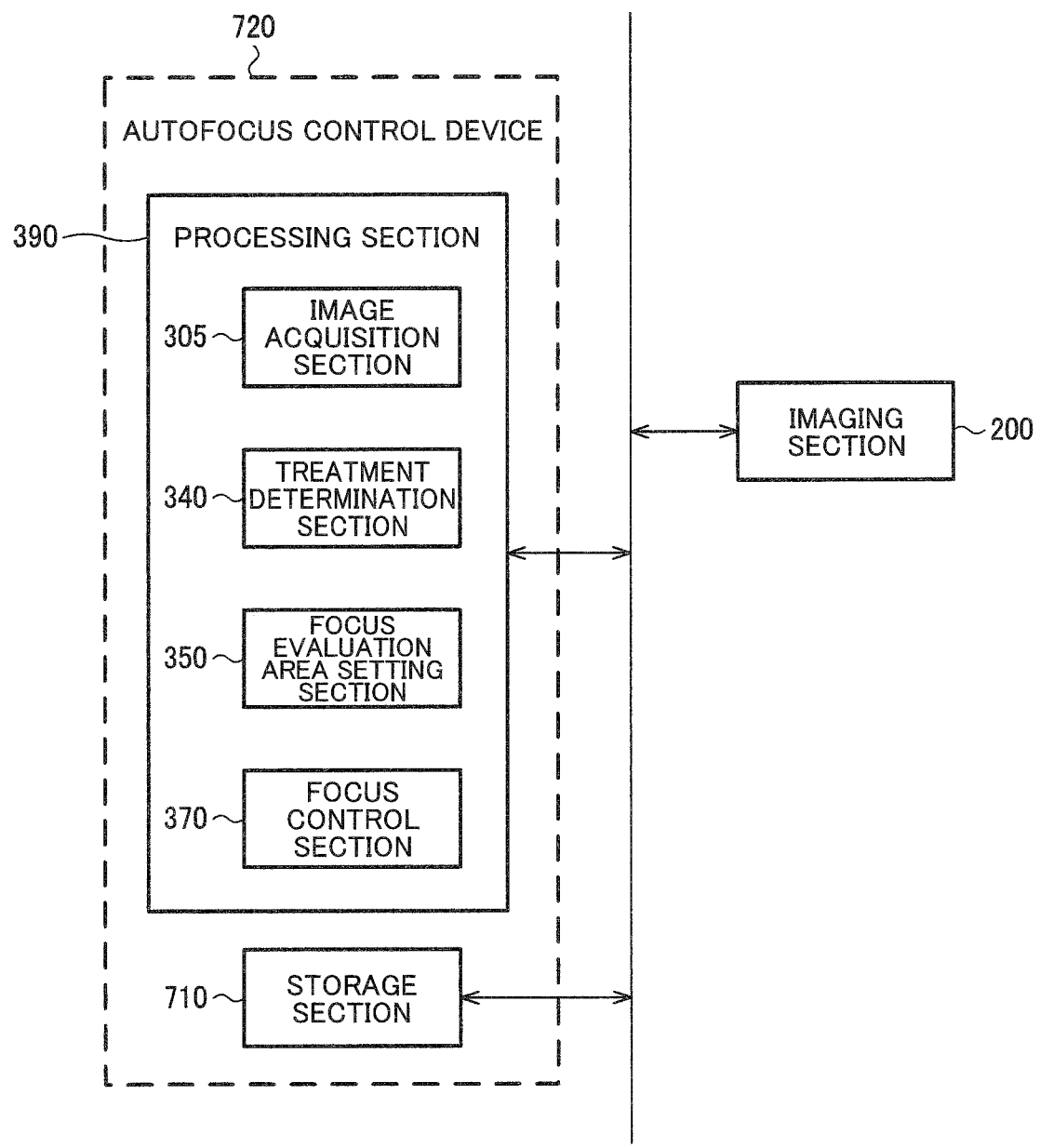
FIG. 1 illustrates a configuration example of an endoscope apparatus.

FIG. 1 illustrates a configuration example of an endoscope apparatus. The endoscope apparatus includes an autofocus control device 720 and an imaging section 200 (imaging device). The autofocus control device 720 includes a processing section 390 (processing circuit or processing device) and a storage section 710 (storage device or memory). The processing section 390 includes an image acquisition section 305, a treatment determination section 340, a focus evaluation area setting section 350, a focus evaluation value calculation section 360, and a focus control section 370 (AF control section).

Note that this embodiment is not limited to the configuration illustrated in FIG. 1, and may be modified in various ways with some of the components omitted or other components added. For example, the autofocus control device 720 may include the imaging section 200 and the storage section 710 may be disposed outside the autofocus control device 720.

The image acquisition section 305 acquires an object image captured by the imaging section 200. The treatment determination section 340 determines whether or not treatment is being performed based on the object image. Based on a determination result of the treatment determination section 340, the focus evaluation area setting section 350 sets either the preset area or the treatment area that is set based on the object image as the focus evaluation area in the object image. The focus control section 370 performs focus control of the imaging section 200 based on a focus evaluation value of the focus evaluation area.

The object image is an image of an object that the imaging section 200 is taking and is an image (image data or image signal) captured by imaging by the imaging section 200 (image sensor). For example, regarding a surgical endoscope, an object is a living body (including a body of a human and an animal) such as an organ and tissue inside the living body.

The determination of whether or not the treatment is being performed is a determination of whether or not any sort of treatment is being performed on an area (object) shown in the object image. For example, it does not matter where the treatment is being performed, as long as it is in the area shown in the object image. The treatment is an act that has some sort of effect on the organ or the tissue of the living body, and treatment with a treatment tool (such as a forceps, an energy device and a knife) is assumed for example.

The preset area is an area where a shape, a position and a size are set in advance. For example, setting information for setting the preset area is stored in the storage section 710 and the focus evaluation area setting section 350 sets the preset area based on the setting information. The preset area is an area (the center area of the image) that is set to enable overall focusing on the surgical field, in accordance with the recommendation that the surgical field be introduced into the center of a field of view in the laparoscopic surgery.

The treatment area is an area where the treatment is being performed on the object. That is, it is where some sort of change is caused to the object by an act of the treatment tool to the object. For example, it is an area where the object is moving due to the treatment, where color and luminance are changing (for example, bleeding) due to the treatment, or the like.

The focus evaluation value is an evaluation value for evaluating a focus status or a focusing level. For example, as the focus evaluation value, a contrast value, an edge quantity, or the like may be used. The focus control is control (AF control) for automatically focusing on the focus evaluation area using the focus evaluation value.

According to this embodiment, depending on whether or not the treatment is being performed, the preset area or the treatment area can be automatically focused. Therefore, if the user desires to see the object of the treatment entirely, the preset area is selected as the focus evaluation area and the object of the treatment is focused entirely. On the other hand, when a pinpoint treatment area is important, the treatment area is selected as the focus evaluation area and the pinpoint treatment area is focused.

Specifically, if it is determined that the treatment is not being performed, the focus evaluation area setting section 350 sets the preset area as the focus evaluation area. On the other hand, if it is determined that the treatment is being performed, the focus evaluation area setting section 350 detects the treatment area where the treatment is being performed on an object based on the object image, and sets the treatment area thus detected as the evaluation area.

With this configuration, when the treatment is not being performed, the preset area is selected as the focus evaluation area and the object of the treatment is focused entirely. On the other hand, when the treatment is being performed, the treatment area is selected as the focus evaluation area and the treatment area is focused at a pinpoint. Accordingly, the user can confirm the surgical field entirely before the treatment, and when performing the treatment, the user can treat on the treatment area that is always in-focus wherever it is.

Figure 5:
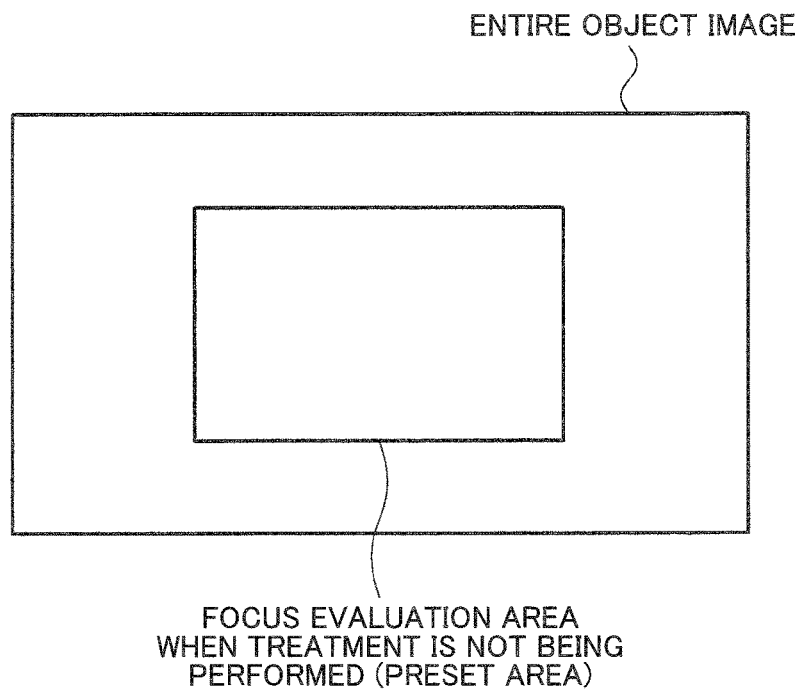
FIG. 5 illustrates an example of a focus evaluation area set when treatment is not being performed.

Moreover, in this embodiment, as shown in FIG. 5, the preset area is an area in a predetermined size including the center of the object image.

The center of the object image is the central position of the object image and is a middle point of the width in a horizontal direction and a middle point of the length in a vertical direction of the object image, for example. The area in the predetermined size is smaller than a size of the object image. For example, the preset area is square or rectangular, the width in the horizontal direction of which is smaller than the width in the horizontal direction of the object image, and the length in the vertical direction of which is smaller than the length in the vertical direction of the object image. For example, the width in the horizontal direction of the preset area is about 50% of the width in the horizontal direction of the object image, while the length in the vertical direction of the preset area is about 50% of the length in the vertical direction of the object image. Note that the size of the preset area is not limited to this.

The area including the center of the object image is an area in which the center of the object image is located at some (arbitrary) position. That is, as long as the center of the object image is included in the preset area, the center of the object image may be anywhere in the preset area. Preferably, the center of the preset area is set adjacent to the center of the object image (for example, within 10% of the width of the object image). For example, preferably, the position of the center of the preset area is set such that a circumference of the preset area (boundary or sides) is inside a circumference (sides) of the object image.

As described above, the preset area is an area that is set adjacently to the center of the object image in advance and has a predetermined size. Setting such a preset area as the focus evaluation area makes it possible to focus on an adjacent area of the center of the object image entirely.

Moreover, in this embodiment, an area of the treatment area is smaller than an area of the preset area.

For example, in an example described later with reference to FIG. 3, if a total count (the number of pixels whose changes in pixel values are detected) is larger than a count threshold value 2, it is determined that the treatment is not being performed in a step S8. Alternatively, in an example described later with reference to FIG. 4, if a total count (the number of motion vectors whose differences from peripheral motion vectors are detected) is larger than a count threshold value 4, it is determined that the treatment is not being performed in a step S28. That is, it is determined that the treatment is being performed only if changes in the image are detected in an area equal to or smaller than a predetermined area. If it is determined that the treatment is being performed, a change area (treatment area) is detected as described later in an example with reference to FIG. 7. However, since it is determined that the treatment is being performed when the changes in the image are detected in the area equal to or smaller than the predetermined area, an area of the change area thus detected ought to be equal to or smaller than the predetermined area. In this way, the area of the treatment area can be controlled to be smaller than the area of the preset area.

During the treatment, a pinpoint focus on the object of the treatment is desired, and thus the focus evaluation area is preferably small. In this regard, according to this embodiment, the area of the treatment area is smaller than the area of the preset area, thereby enabling the pinpoint focus on the object of the treatment during the treatment.

Moreover, in this embodiment, the treatment determination section 340 determines whether or not the treatment is being performed based on a local image change in the object image.

The image change is a change caused between a previous frame and a current frame. For example, it is movement of the image (object) and a change in color and luminance of the image (object). The local image change is a change caused in a partial area of the image. That is, it is not a change of the entire image caused by a relative movement between a camera and the object for example, but a change in a partial area of the image with the rest of the area unchanged.

When the treatment is performed on the object of the treatment, it is assumed that changes would be caused locally on the object. In this embodiment, the local image change in the object image is detected, thereby enabling the determination of whether or not the treatment is being performed on the object. Furthermore, when the object image changes entirely, it is highly possibility that the change is not caused by the treatment. Therefore, detecting the local image change enables exclusion of the change not caused by the treatment.

Moreover, in this embodiment, the treatment determination section 340 determines that the treatment is being performed if the area of where the local image change is determined to exist is within a predetermined range.

Figure 3:
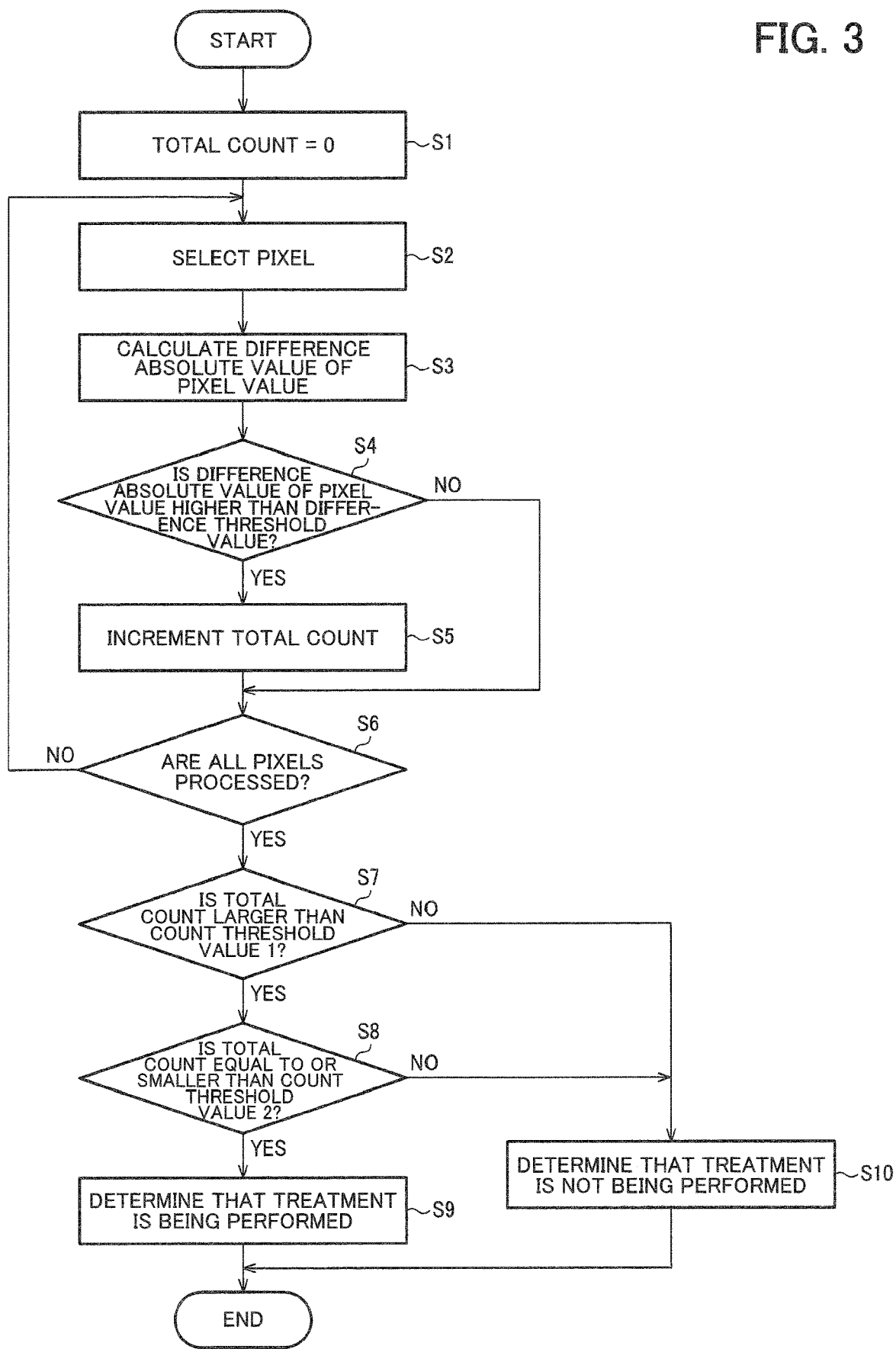
FIG. 3 is a first flowchart illustrating procedures of a process performed by a treatment determination section.

For example, as shown in steps S7 to S10 in FIG. 3, if the total count (number of pixels whose changes in the pixel values are detected) is between a count threshold value 1 and a count threshold value 2, it is determined that the treatment is being performed. Alternatively, as shown in steps S27 to S30 in FIG. 4, it is determined that the treatment is being performed if the total count (the number of motion vectors determined to indicate local motion) is between a count threshold value 3 and a count threshold value 4. These methods enable the determination of whether or not the area of where the local image change is determined to exist is within the predetermined range.

If the area of where the local image change is determined to exist is small, influence of noise is assumed. On the other hand, if the area of where the local image change is determined to exist is large, influence of movement of the camera or generation of mist or the like is assumed. As described above, there are image changes caused by factors other than the treatment, and these image changes may cause an erroneous determination that the treatment is being performed. Regarding this point, in this embodiment, it is determined that the treatment is being performed if the area of where the local image change is determined to exist is within the predetermined range (it is determined that the treatment is not being performed if the area is not within the predetermined range), thereby preventing the erroneous determination that the treatment is being performed based on the image changes due to the factors other than the treatment as described above.

Moreover, in this embodiment, the treatment determination section 340 determines whether or not the local image change exists based on a time change in the pixel value of the object image, or a difference between a motion amount (a motion amount of a process target out of motion amounts obtained in a plurality of places) and a peripheral motion amount in a periphery of a position where the motion amount is obtained.

The time change in the pixel value is a change in the pixel value caused between the previous frame and the current frame such as a difference (or a value based on the difference) between a pixel value in the previous frame and a pixel value in the current frame. More specifically, it is a change in the pixel value of the same pixel (or a neighboring pixel) caused between the previous frame and the current frame.

The motion amount is an amount representing motion of the image caused between the previous frame and the current frame. For example, it is a motion vector (an amount representing a magnitude and a direction of the motion). Note that it is not limited to this and may be an amount representing only a magnitude of the motion or an amount representing only a direction of the motion. The peripheral motion amount in the periphery of the position where the motion amount is obtained is a motion amount of a position adjacent to a position of a certain motion amount (or a motion amount at a position included in a predetermined area defined based on a position of a motion amount of a process target) when motion amounts are obtained at discrete positions in the image, for example.

When a local movement of the object or a local change in color and luminance of the object is caused, the time change in the pixel value is generated. That is, detecting the time change in the pixel value enables the determination of whether or not the local image change exists. In addition, if a local movement of the object is caused, a difference between a motion amount at that position and a peripheral motion amount in the periphery of that position is not zero. That is, detecting the difference between the motion amount and the peripheral motion amount in the periphery of the position where the motion amount is obtained enables the determination of whether or not the local image change exists.

Moreover, in this embodiment, the focus evaluation area setting section 350 sets the treatment area where the treatment is being performed on the object based on the local change in the object image.

As described above, it is assumed that the local image change would be caused in the area where the treatment is being performed. In this embodiment, the treatment area is set based on the local change in the object image, thereby enabling setting the area where the treatment is being performed on the object as the treatment area (focus evaluation area).

Note that the treatment area may be set at any position in the image regardless of a setting position of the preset area. For example, depending on an inserting position of a scope, arrangement of organs or a position of an object of the treatment, the object of the treatment may not be framed in the center of a field of view. In such cases, the treatment has to be performed at a periphery of the image (an area near an edge). In this embodiment, the treatment area is set as the focus evaluation area instead of the preset area during the treatment, thereby enabling an appropriate auto-focusing on the object of the treatment even if the object of the treatment is not in the center of the screen.

Moreover, in this embodiment, the focus evaluation area setting section 350 performs processing for detecting the local image change on the object image, and sets the area where the local image change is detected as the treatment area.

With this configuration, the area where the local image change is caused by the treatment can be detected as the treatment area. That is, it is possible to detect a pinpoint area where the treatment is being performed and focus on that area during the treatment.

Furthermore, in this embodiment, the focus evaluation area setting section 350 detects the treatment area based on the time change in the pixel value in the object image, or the difference between the motion amount and the peripheral motion amount in the periphery of the position where the motion amount is obtained.

As described above, when a local movement of the object or a local change in color and luminance of the object is caused, the time change in the pixel value is generated. That is, detecting the time change in the pixel value enables detection of the area where the local image change is caused. In addition, as described above, if the local movement of the object is caused, a difference between a motion amount at that position and a peripheral motion amount in a periphery of that position is not zero. That is, detecting the difference between the motion amount and the peripheral motion amount in the periphery of the position where the motion amount is obtained enables the detection of the area where the local image change is caused.

Moreover, in this embodiment, the focus evaluation area setting section 350 sets an area where the treatment area is expanded as the focus evaluation area, when setting the treatment area as the evaluation area.

In an example described later with reference to FIG. 7, a change area is detected in a step S42 and the treatment area (focus evaluation area) is set based on the change area. At this time, expanding the change area in the step S42 corresponds to the expansion of the treatment area.

When the change in the object due to the treatment is small, the area of the treatment area (focus evaluation area) becomes small. In this case, the focus evaluation value may not be calculated accurately, and thus an appropriate AF may not be performed (for example, a focus state changes unstably). In addition, when a place of the treatment is suddenly changed, a distance to the treatment area suddenly changes, and thus an appropriate AF my not be performed (for example, focusing operation cannot follow). In this regard, according to this embodiment, expanding the treatment area enables an accurate calculation of the focus evaluation value. Alternatively, a sudden change of the focus evaluation value can be suppressed. With this configuration, an appropriate AF (stable AF) can be implemented.

Specifically, the focus evaluation area setting section 350 sets the focus evaluation area to the area where the treatment area is spatially expanded or an area set based on a previous treatment area, as the area where the treatment area is expanded.

The area where the treatment area is spatially expanded is an area where a boundary of the treatment area detected based on the local image change is expanded outward (where the area of the treatment area is expanded). The area set based on a previous treatment area is an area set in a current frame based on the treatment area detected in a previous frame. For example, the same area as the treatment area detected in the previous frame is set as the treatment area in the current frame.

Accordingly, setting the area where the treatment area is spatially expanded as the focus evaluation area makes the area of the treatment area larger even if the change in the object caused by the treatment is small, and thus enables an appropriate AF. In addition, setting the area set based on the previous treatment area as the focus evaluation area can suppress a sudden change in the focus evaluation value even if the position of the treatment is suddenly changed, and thus enables an appropriate AF.

Furthermore, in this embodiment, the focus evaluation area setting section 350 sets an area where a treatment tool area is eliminated from the preset area as the focus evaluation area, when setting the preset area as the focus evaluation area. Furthermore, in this embodiment, the focus evaluation area setting section 350 sets an area where the treatment tool area is eliminated from the treatment area as the focus evaluation area, when setting the treatment area as the focus evaluation area.

An example of setting the treatment area as the focus evaluation area will be described later with reference to FIG. 7. In this example, the change area is detected in the step S42, the treatment tool area is eliminated from the change area and a resultant area is set as the focus evaluation area (treatment area) in steps S43 to S46.

During the treatment, the treatment tool also moves, and thus it is presumed that the area where the local image change is detected includes the treatment tool. However, if the autofocus process is performed on the area including the treatment tool and the object of the treatment, the treatment tool may be in focus. At this time, since a distance to the treatment tool and a distance to the object of the treatment are different, once the treatment tool is in focus, the object of the treatment may be out of focus (may be outside the depth of field or may be blur) in the case that the depth of field of the imaging section is shallow. In this regard, according to this embodiment, the focus evaluation area (treatment area) is set without the treatment tool area, and thus the focus evaluation area includes only the object of the treatment, thereby enabling an appropriate focusing on the object of the treatment.

Figure 7:
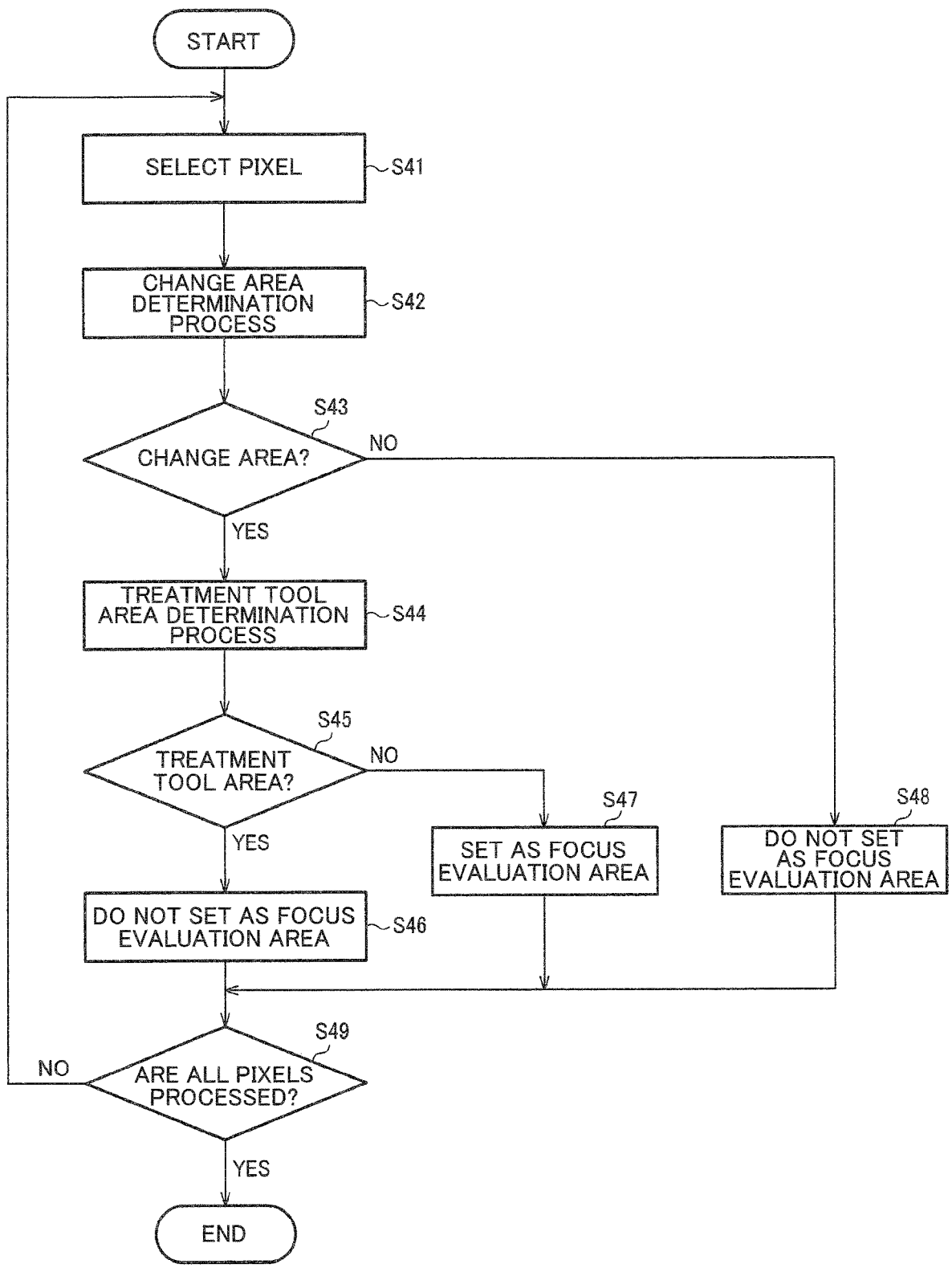
FIG. 7 is a flowchart illustrating procedures of a process performed by a focus evaluation area setting section if it is determined that treatment is being performed.

When the preset area is set as the focus evaluation area, the treatment tool area can be detected by the same method as that shown in the step S45 in FIG. 7 for example, and can be eliminated from the preset area. Even in this case, once the treatment tool is in focus, an organ or tissue (object of the treatment or observation) in the preset area that is originally desired to be focused may be out of focus. In this regard, according to this embodiment, the focus evaluation area is set without the treatment tool area, and thus the focus evaluation area includes only the organ or the tissue, thereby enabling an appropriate focusing on the organ or the tissue in the preset area.

Moreover, in this embodiment, the focus evaluation area setting section performs a process for detecting a local image change in the object image and a process for detecting the treatment tool area, and sets an area where the treatment tool area is eliminated from an area where the local image change is detected as the focus evaluation area, when setting the treatment area as the focus evaluation area.

With this configuration, the treatment tool area can be eliminated from the area where the local image change is detected including the treatment tool. Accordingly, the focus evaluation area (treatment area) without the treatment tool can be in focus.

Furthermore, in this embodiment, the focus control section 370 changes a control parameter for the focus control according to the determination result of the treatment determination section 340.

The control parameter is a parameter for setting focus operation (operation for focusing on the focus evaluation area) controlled by the focus control (AF control). That is, if the control parameter is changed, the focus operation (some sort of operation in the focus control) is changed accordingly.

The object to be focused differs between a case where the treatment is being performed (a case where the treatment area is focused) and a case where the treatment is not being performed (a case where the preset area is focused), and thus different focus control may be appropriate in some cases. In this embodiment, changing the control parameter for the focus control according to a determination result of the treatment determination section 340 enables an implementation of an appropriate focus control depending on whether or not the treatment is being performed.

Specifically, the focus control section 370 performs a focus completion determination for determining whether or not autofocus operation is completed, and if the autofocus operation is determined to be completed, the focus control section 370 stops the autofocus operation and changes the control parameter of the focus completion determination according to the determination result of the treatment determination section 340.

In an example described later with reference to FIG. 9, overall flowchart in FIG. 9 corresponds to the focus completion determination while a control parameter for wobbling operation corresponds to the parameter for the focus control. For example, a lens position threshold value used by a turn frequency reset determination process in steps S64 and S65 corresponds to the control parameter. Alternatively, an in-focus lens position set by an in-focus lens position setting in a step S69 corresponds to the control parameter.

Figure 9:
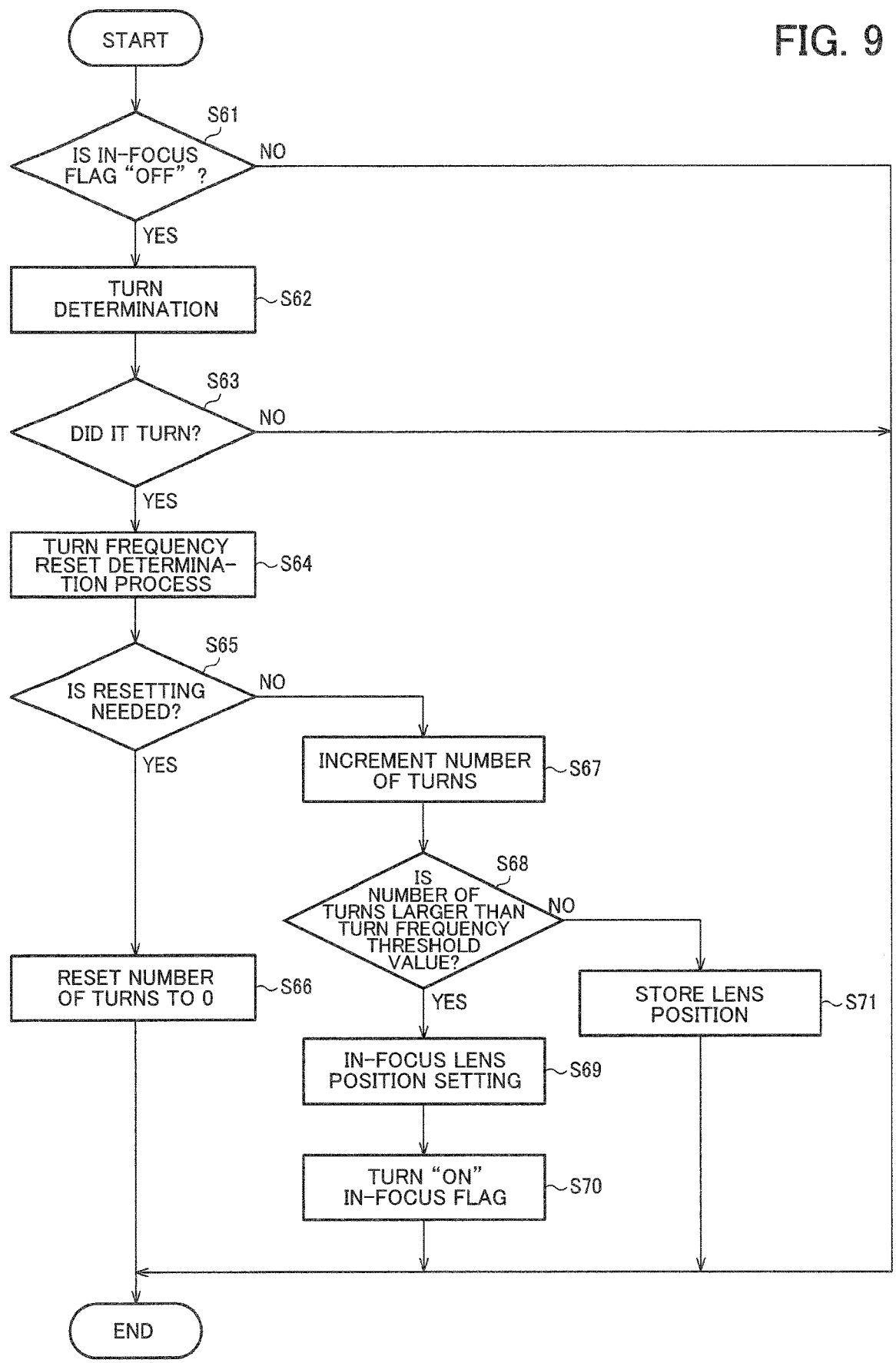
FIG. 9 is a flowchart illustrating procedures of a process performed by a focus control section.

As described above, changing the control parameter in the focus completion determination depending on whether or not the treatment is being performed enables, for example, a change in a condition to stop the AF (a condition to stop the AF is changed by changing a condition to reset the number of turns in FIG. 9) and a change in a setting when the AF is stopped (a setting of the focus lens position when the AF is stopped is changed in FIG. 9).

The example in which the focus evaluation area is switched depending on whether or not the treatment is being performed is described above, however, this embodiment is not limited to this and may include a configuration and operation as follows.

That is, the image acquisition section 305 acquires the object image captured by the imaging section 200. The focus evaluation area setting section 350 detects the treatment area in the object image based on the object image, and sets the treatment area thus detected as the focus evaluation area. The focus control section 370 performs the focus control of the imaging section 200 based on the focus evaluation value of the focus evaluation area.

With this configuration, it is possible to detect the treatment area where the treatment is being performed on the object and focus on the treatment area at a pinpoint. Accordingly, even if a large number of pixels or the like makes the depth of field shallower, implementation of an in-focus state on the treatment area is enabled, thereby facilitating the treatment by the user.

Moreover, the autofocus control device according to the present embodiment may have a configuration described below. That is, the autofocus control device includes a memory configured to store information (for example, a program and various types of data) and a processor (processor including hardware) configured to operate based on the information stored in the memory. The processor acquires the object image captured by the imaging section 200, determines whether or not the treatment is being performed based on the object image, sets either the preset area or the treatment area set based on the object image as the focus evaluation area in the object image based on the determination result of whether or not the treatment is being performed, and performs the focus control of the imaging section 200 based on the focus evaluation value of the focus evaluation area.

For example, the processor may have functions of sections each implemented by individual hardware, or the functions of sections each implemented by integrated hardware. For example, the processor may include hardware, and the hardware may include at least one of a circuit that processes a digital signal and a circuit that processes an analog signal. For example, the processor may include one or a plurality of circuit devices (such as an integrated circuit (IC) for example) mounted on a circuit board, or one or a plurality of circuit elements (such as a resistor and a capacitor for example). The processor may be a central processing unit (CPU), for example. Note that the processor is not limited to a CPU, but various other processors such as a graphics processing unit (GPU) or a digital signal processor (DSP) may also be used. The processor may be a hardware circuit that includes an application specific integrated circuit (ASIC). The processor may include an amplifier circuit or a filter circuit that processes an analog signal. The memory (storage section 710 in FIG. 1 for example) may be a semiconductor memory such as a SRAM or a DRAM, or may be a register. The memory may be a magnetic storage device such as a hard disk drive, or may be an optical storage device such as an optical disc device, for example. For example, the memory stores a computer-readable instruction, and the function of each section of the autofocus control device (for example, the autofocus control device 720 in FIG. 1, or the processing section 300 in FIG. 2) is implemented by causing the processor to perform the instruction. The instruction may be an instruction set that is included in a program, or may be an instruction that instructs the hardware circuit included in the processor to operate.

For example, operations according to the present embodiment are implemented as follows. The object image acquired by the imaging section 200 is stored in the memory. The processor reads out the object image from the memory, determines whether or not the treatment is being performed based on the object image and stores the determination result into the memory. The processor reads out the determination result from the memory, sets either the preset area or the treatment area set based on the object image as the focus evaluation area in the object image based on the determination result, and stores the setting information of the focus evaluation area into the memory. The processor reads out the setting information of the focus evaluation area from the memory, sets the focus evaluation area based on the setting information, and performs the focus control of the imaging section 200 based on the focus evaluation value of the focus evaluation area.

In addition, the sections of the autofocus control device (for example, the autofocus control device 720 in FIG. 1 or the processing section 300 in FIG. 2) according to this embodiment may be implemented as modules of a program operating on the processor. For example, the image acquisition section 305 is implemented as an image acquisition module configured to acquire the object image captured by the imaging section 200. The treatment determination section 340 is implemented as a treatment determination module configured to determine whether or not treatment is being performed based on the object image. The focus evaluation area setting section 350 is implemented as a focus evaluation area setting module configured to set either the preset area or the treatment area set based on the object image as the focus evaluation area in the object image based on the determination result of the treatment determination section 340. The focus control section 370 is implemented as a focus control module configured to perform the focus control of the imaging section 200 based on the focus evaluation value of the focus evaluation area.

2. Endoscope Apparatus

Figure 2:
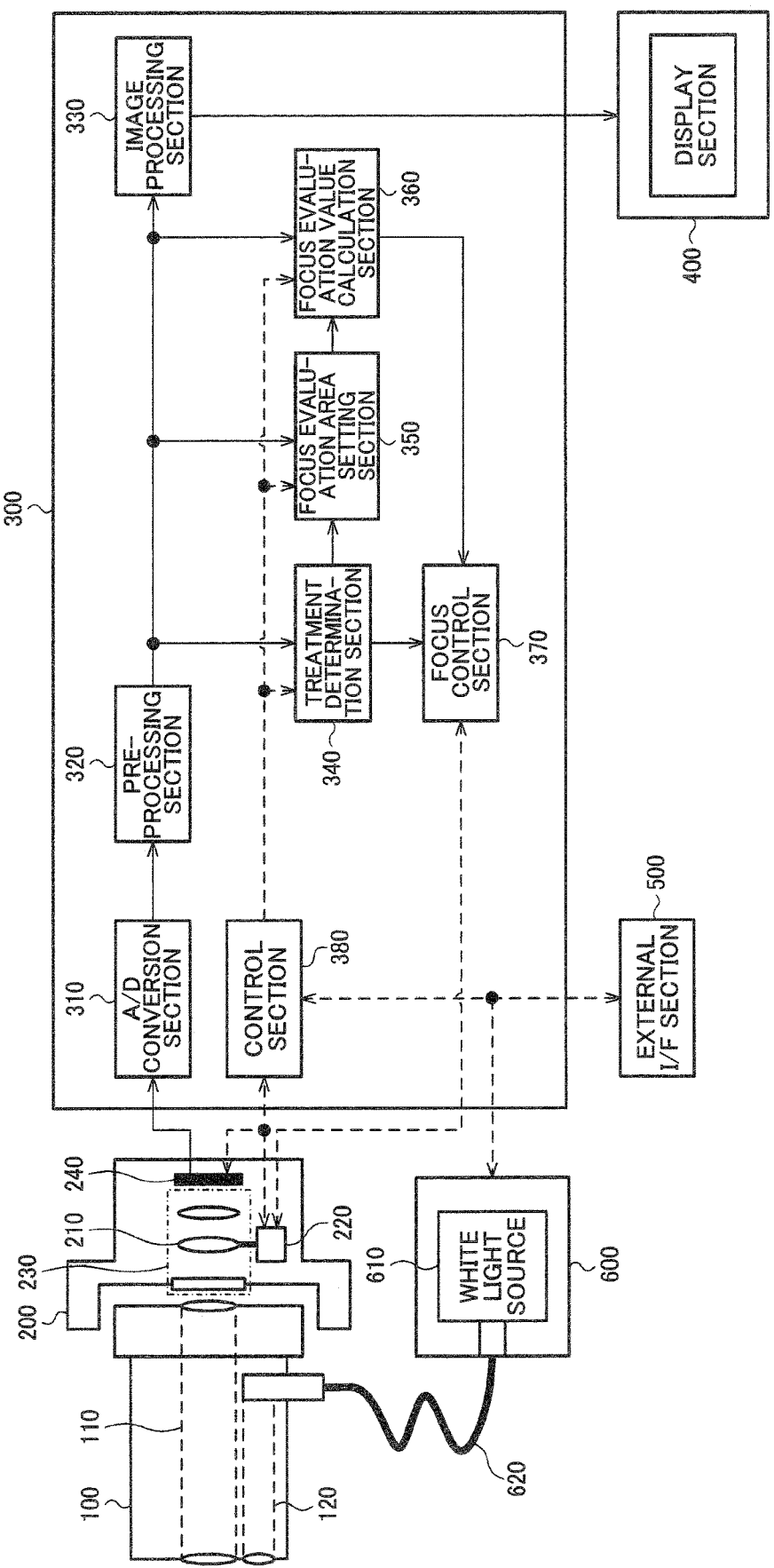
FIG. 2 illustrates a detailed configuration example of the endoscope apparatus.

FIG. 2 illustrates a detailed configuration example of the endoscope apparatus (surgical endoscope apparatus). The endoscope apparatus includes a rigid scope 100, the imaging section 200 (imaging device), the processing section 300 (processing device and control device), a display section 400 (display device), an external I/F section 500 (interface), and a light source section 600 (light source device).

For example, the rigid scope 100, the imaging section 200, the processing section 300, the display section 400, and the light source section 600 are respectively provided as a rigid scope, a camera head, a video processor (processing device), a display, and a light source device as individual devices. The rigid scope is detachably attached to the camera head with a chuck mechanism provided to the camera head. The camera head, the display, and the light source device are each connected to the video processor via a cable. The rigid scope is connected to the light source device via a light guide cable. Note that the configurations of the imaging device and the endoscope apparatus are not limited to this.

Configurations and operation of the sections are described below. Note that the processing section 300 in FIG. 2 corresponds to the autofocus control device 720 in FIG. 1. The storage section 710 is omitted in FIG. 2.

The rigid scope 100 is inserted into the body. The rigid scope 100 includes a lens system 110 (optical device or lens) and a light guide section 120 (light guide).

The lens system 110 is an optical device including a plurality of lenses such as an imaging lens, a relay lens, an eyepiece, and the like. The light source section 600 includes a white light source 610 and let light emitted from the while light source 610 enter a light guide cable 620. The light guide section 120 guides light emitted from the light guide cable 620 to a distal end of the rigid scope 100.

The imaging section 200 forms an image from reflected light from the object. The imaging section 200 includes a focus lens 210, a focus lens driving section 220 (focus lens driving device), an objective lens system 230 (objective lens), and an image sensor 240.

The focus lens 210 is a lens for adjusting an in-focus object plane position (focus). The focus lens driving section 220 drives the focus lens 210 (moves the position of the focus lens 210). The focus lens driving section 220 is a voice coil motor (VCM), for example. The objective lens system 230 forms an optical image from reflected light that is light emitted from the light guide section 120 and reflected on the object (forms an optical image of the object). The image sensor 240 photoelectrically converts the reflected light for forming the optical image with the objective lens system 230 into an image.

The processing section 300 performs signal processing including image processing. The processing section 300 includes the image acquisition section 305, an A/D conversion section 310 (A/D conversion circuit), a pre-processing section 320 (pre-processing circuit), an image processing section 330 (image processing circuit), the treatment determination section 340 (treatment determination circuit), the focus evaluation area setting section 350 (focus evaluation value calculation circuit), the focus evaluation value calculation section 360 (focus evaluation value calculation circuit), the focus control section 370 (AF control section or focus control circuit), and a control section 380 (control circuit). Note that the A/D conversion section 310, the pre-processing section 320 or both of them in FIG. 2 correspond to the image acquisition section 305 in FIG. 1.

The A/D conversion section 310 converts analog signals sequentially output from the image sensor 240 into digital images and sequentially outputs the digital images to the pre-processing section 320.

The pre-processing section 320 performs image processing including a white balance process, an interpolation process (demosaicing process), and the like on the images output from the A/D conversion section 310, and sequentially outputs the resultant images to the image processing section 330, the treatment determination section 340, the focus evaluation area setting section 350, and the focus evaluation value calculation section 360. The image processing section 330 performs image processing including a color conversion process, a grayscale transformation process, an edge enhancement process, a scaling process, a noise reduction, and the like on the images output from the pre-processing section 320, and sequentially outputs the resultant images to the display section 400.

The treatment determination section 340 determines whether or not the treatment is being performed based on the image output from the pre-processing section 320. That is, the treatment determination section 340 determines whether or not the treatment is being performed on the object in the image based on the image. The treatment determination section 340 outputs a determination result to the focus evaluation area setting section 350 and the focus control section 370. The treatment determination section 340 will be described later in detail with reference to FIG. 3 and FIG. 4. Additionally, the treatment determination section 340 may determine whether or not the treatment is being performed based on control signals emitted when an energy device, not shown, is used. The energy device is a device (treatment tool) to cut or stop bleeding of the object of the treatment by applying some sort of energy to the object of the treatment (tissue or organ) such as an electrosurgical knife that applies electric current to the object of the treatment and an ultrasonic surgical knife that applies ultrasonic waves to the object of the treatment. The treatment determination section 340 may use the control signals for turning on or off energy application so as to determine that the treatment is being performed if it is on and that the treatment is not being performed if it is off.

The focus evaluation area setting section 350 sets the focus evaluation area on the image output from the pre-processing section 320, and outputs the resultant to the focus evaluation value calculation section 360. However, based on the determination result from the treatment determination section 340, when the treatment is not being performed, the focus evaluation area setting section 350 sets the preset area (center of the screen) as the focus evaluation area. On the other hand, when the treatment is being performed, the focus evaluation area setting section 350 sets an automatically detected area as the focus evaluation area. The focus evaluation area will be described later in detail with reference to FIG. 5 and FIG. 6. The focus evaluation area setting section 350 will be described later in detail with reference to FIG. 7.

The focus evaluation value calculation section 360 calculates the focus evaluation value from the image in the focus evaluation area and outputs the focus evaluation value to the focus control section 370. For example, the focus evaluation value calculation section 360 performs a band-pass filter process on the image and uses the output as the focus evaluation value.

The focus control section 370 controls the focus lens driving section 220 so as to focus on the object (object in the focus evaluation area) based on the focus evaluation value output from the focus evaluation value calculation section 360. As an autofocus method, any one of various methods such as a wobbling method and a contrast method (hill climbing method) may be adopted. However, based on the determination result of whether or not the treatment is being performed output from the treatment determination section 340, the control parameter for the focus control is modified. The focus control section 370 will be described later in detail with reference to FIG. 8 and FIG. 9.

The control section 380 is bidirectionally connected to the external I/F section 500, the image processing section 330, the focus control section 370, the image sensor 240, and the like, and exchanges a control signal with them.

The display section 400 sequentially displays the object images output from the image processing section 330. The display section 400 is a display device (display) such as a liquid crystal monitor.

The external I/F section 500 is an interface used for input to the endoscope apparatus by the user or the like. For example, the external I/F section 500 includes an adjustment button for adjusting a parameter for the image processing.

3. Treatment Determination Section

FIG. 3 is a first flowchart illustrating procedures of a process performed by the treatment determination section 340. In FIG. 3, the treatment determination section 340 determines whether or not the treatment is being performed based on a change in the pixel value. That is, the treatment determination section 340 counts the number of pixels whose changes in the pixel values between the previous frame and the current frame are larger than a certain value, and if the total count is within a certain range, determines that the treatment is being performed.

Specifically, when the process starts, the total count is reset to 0 (S1). Next, a pixel is selected from the image (S2). Next, a difference absolute value between the pixel values of the pixel thus selected in the previous frame and the current frame is calculated (S3). The previous frame is an immediately preceding frame of the current frame, for example.

Next, the difference absolute value of the pixel value and a difference threshold value are compared. If the difference absolute value of the pixel value is higher than the difference threshold value, the total count is incremented (S5), and if the difference absolute value of the pixel value is equal to or smaller than the difference threshold value, the total count is not incremented. Next, whether or not the process of the steps S2 to S5 has been completed on all of the pixels in the image is determined (S6). If it has not been completed yet, the process returns to the step S2.

If it has been completed, whether or not the total count is larger than a count threshold value 1 (first count threshold value) is determined (S7). If the total count is equal to or smaller than the count threshold value 1, it is determined that the treatment is not being performed (S10). If the total count is larger than the count threshold value 1, whether or not the total count is equal to or smaller than a count threshold value 2 (second count threshold value) is determined (S8). The count threshold value 2 is larger than the count threshold value 1 and smaller than a total number of pixels in the image. If the total count is larger than the count threshold value 2, it is determined that the treatment is not being performed (S10). If the total count is equal to or smaller than the count threshold value 2, it is determined that the treatment is being performed (S9).

As described above, the treatment determination section 340 determines that the treatment is being performed if the total count is larger than the count threshold value 1 and equal to or smaller than the count threshold value 2. Otherwise, the treatment determination section 340 determines that the treatment is not being performed. When the treatment is being performed, due to the operation of the treatment tool, the difference absolute value of the pixel value between the frames becomes higher than a certain value in pixels of more than a certain number. Therefore, this threshold value determination using the count threshold value 1 can suppress an erroneous determination due to influence of noise. That is, even if the total count increases due to the noise, it can be determined that the treatment is not being performed as long as the total count is equal to or smaller than the count threshold value 1. In addition, even if the treatment is not being performed, a pan (horizontal panning of a direction of a camera) or a tilt (vertical panning of a direction of a camera) of a camera of the endoscope apparatus causes the difference absolute value of the pixel value between the frames to be equal to or higher than a certain value in many pixels. Therefore, the threshold value determination using the count threshold value 2 can suppress erroneous determinations due to pan operation and tilt operation. That is, in the pan and tilt operation, the difference absolute value of the pixel value becomes equal to or higher than a certain value in most of the pixels, and thus if the total count is larger than the count threshold value 2, it can be determined that the treatment is not being performed.

Figure 4:
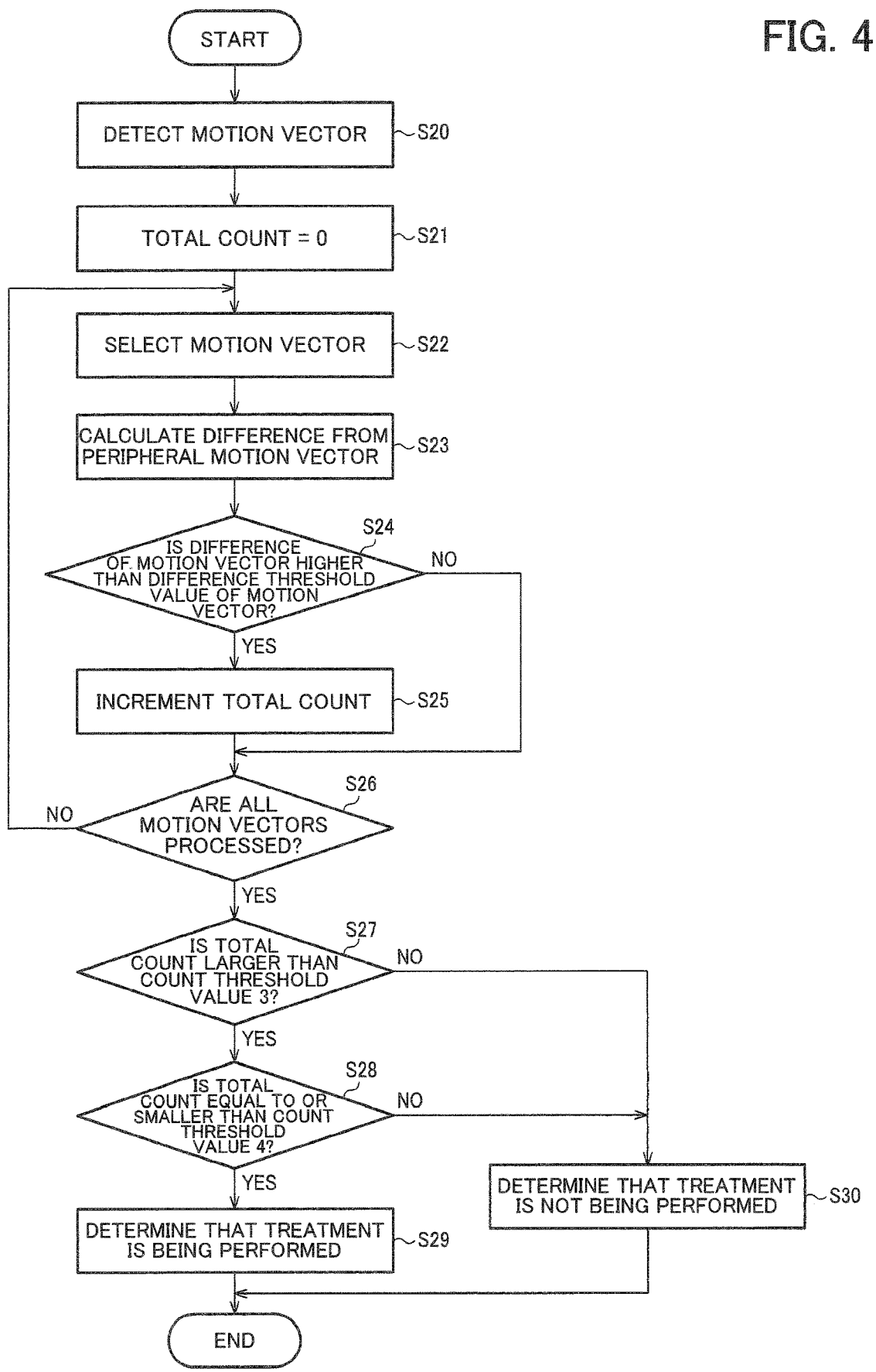
FIG. 4 is a second flowchart illustrating procedures of a process performed by a treatment determination section.

FIG. 4 is a second flowchart illustrating procedures of a process performed by the treatment determination section 340. In FIG. 4, the treatment determination section 340 determines whether or not the treatment is being performed based on a motion vector. That is, the treatment determination section 340 detects a motion vector between the previous frame and the current frame and determines that the treatment is being performed if the number of motion vectors indicating local differences from peripheral motion vectors is within a certain range.

Specifically, when the process starts, the motion vectors between the previous frame and the current frame are detected (S20). For example, the motion vectors are detected from pixels by pixels in a predetermined interval in a horizontal direction and in a predetermined interval in a vertical direction. Next, total count is reset to 0 (S21). Next, a motion vector is selected from a plurality of motion vectors detected in the image (S22). Next, a difference (difference absolute value) between the motion vector thus selected and a peripheral motion vector in a periphery of the selected motion vector is calculated (S23). For example, difference vectors between the selected motion vector and motion vectors on upper, lower, right and left sides of the selected motion vector are respectively obtained and absolute values of these four difference vectors are totaled.

Then, the difference of the motion vector and a difference threshold value of a motion vector are compared to determine whether or not the difference of the motion vector is higher than the difference threshold value of the motion vector (S25). If the difference of the motion vector is higher than the difference threshold value of the motion vector, the total count is incremented (S26). If the difference of the motion vector is equal to or lower than the difference threshold value of the motion vector, the total count is not incremented. Next, whether or not the process of the steps S22 to S25 has been completed on all of the motion vectors in the image is determined (S26). If it has not been completed yet, the process returns to the step S22.

If it has been completed, whether or not the total count is larger than a count threshold value 3 (third count threshold value) is determined (S27). If the total count is equal to or smaller than the count threshold value 3, it is determined that the treatment is not being performed (S30). If the total count is larger than the count threshold value 3, whether or not the total count is equal to or smaller than a count threshold value 4 (fourth count threshold value) is determined (S28). The count threshold value 4 is larger than the count threshold value 3 and smaller than a total number of motion vectors in the image. If the total count is larger than the count threshold value 4, it is determined that the treatment is not being performed (S30). If the total count is equal to or smaller than the count threshold value 4, it is determined that the treatment is being performed (S29).

As described above, the treatment determination section 340 determines that the treatment is being performed if the total count is larger than the count threshold value 3 and equal to or smaller than the count threshold value 4. Otherwise, the treatment determination section 340 determines that the treatment is not being performed. When the treatment is being performed, due to the operation of the treatment tool, the motion vectors more than a certain number indicate the difference larger than a certain degree from the peripheral motion vectors. Therefore, this threshold value determination using the count threshold value 3 can suppress an erroneous determination due to influence of noise. That is, even if the total count increases due to the noise, it can be determined that the treatment is not being performed as long as the total count is equal to or smaller than the count threshold value 3. In addition, even if the treatment is not being performed, when the camera of the endoscope apparatus is panned or tilted, or a large quantity of mist is generated by use of an energy device, the motion vectors become random in the whole image. Accordingly, many motion vectors indicate the differences larger than a certain degree from peripheral motion vectors. Therefore, the threshold value determination using the count threshold value 4 can suppress erroneous determinations due to pan operation, tilt operation and generation of mist. That is, in the pan and tilt operation and the mist generation, most of the motion vectors indicate the differences larger than a certain degree from peripheral motion vectors, and thus, if the total count is larger than the count threshold value 4, it can be determined that the treatment is not being performed.

4. Focus Evaluation Area Setting Section

FIG. 5 illustrates an example of a focus evaluation area set when the treatment is not being performed. As shown in FIG. 5, the preset area is an area defined in the center of the screen (center of the object image) in a predetermined size. For example, the preset area is square or rectangular, the center of the preset area corresponds to the center of the object image (intersection of diagonal lines for example), and top, bottom, right and left sides of the preset area are apart from top, bottom, right and left sides of the object image. If it is determined that the treatment is not being performed, the preset area is set as the focus evaluation area.

It is recommended that the treatment be operated with the object of the treatment framed in the center of the screen in a laparoscopic surgery. For example, at timing before starting the treatment, a user is working to decide a surgical field. In such a timing, setting the preset area as the focus evaluation area makes it possible to focus on a wide area in the center of the image, and thus enables the user to decide the surgical field in the in-focus field of view.

Figure 6:
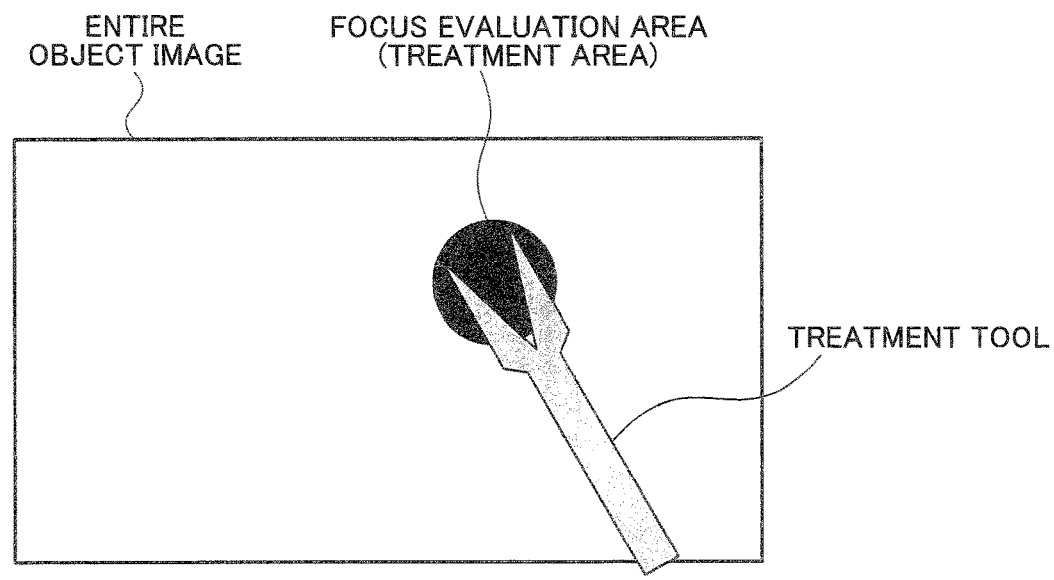
FIG. 6 illustrates an example of a focus evaluation area set when treatment is being performed.

FIG. 6 illustrates an example of the focus evaluation area set when the treatment is being performed. As shown in FIG. 6, if it is determined that the treatment is being performed, the treatment area is set as the focus evaluation area. The treatment area is an area where the object is moved (changed) locally due to operation of a treatment tool (treatment to the object). Note that the treatment tool itself is excluded from the focus evaluation area.

Ideally, a laparoscopic surgery requires an entire abdominal cavity (distance from the endoscope is between tens of millimeters and several hundred millimeters) to be in focus. However, in response to a demand for a large number of pixels for an endoscope in recent years, depth of field is getting shallower, which makes it difficult to focus on the entire abdominal cavity. In addition, even if an organ to be treated seems to be entirely in focus during the treatment, since the depth of field of the endoscope is shallow, there may be an area partially unfocused. When the user treats such an area, since a pinpoint area where the user is treating is not in focus, the user may have difficulty to operate the treatment tool. Regarding this point, in this embodiment, setting the focus evaluation area to the treatment area makes it possible to focus on the pinpoint area of the treatment even by an endoscope with a shallow depth of field.

FIG. 7 is a flowchart illustrating procedures of a process performed by the focus evaluation area setting section 350 if it is determined that the treatment is being performed. As shown in FIG. 7, when the process starts, a pixel is selected from the image (S41). Next, a change area determination process is performed (S42), and determination of whether or not the pixel thus selected belongs to a change area (area where a local movement of the image exists) is performed (S43). For example, the change area determination is made based on the pixel value of the selected pixel. That is, a difference absolute value of the pixel value is calculated as in the step S3 in FIG. 3, and whether or not the difference absolute value of the pixel value is higher than a difference threshold value is determined as in the step S4. If the difference absolute value of the pixel value is higher than the difference threshold value, it is determined that the pixel belongs to the change area, and if the difference absolute value of the pixel value is equal to or lower than the difference threshold value, it is determined that the pixel does not belong to the change area. Alternatively, the change area determination is made based on a motion vector of the selected pixel. That is, differences from peripheral motion vectors are calculated as in the step S23 in FIG. 4, and whether or not the difference of the motion vector is higher than the difference threshold value of the motion vector is determined as in the step S24. If the difference of the motion vector is higher than the difference threshold value, it is determined that the pixel belongs to the change area, and if the difference of the motion vector is equal to or lower than the difference threshold value, it is determined that the pixel does not belong to the change area.

In the step S43, if it is determined that the pixel does not belong to the change area, the pixel is not set as the focus evaluation area (S48). If it is determined that the pixel belongs to the change area, a treatment tool area determination process is performed to determine whether or not the selected pixel belongs to a treatment tool area (area corresponding to the treatment tool) (S44, S45). Since the treatment tool is usually achromatic or in a characteristic color such as green so as to be distinct from a living body, whether or not the pixel belongs to the treatment tool area is determined by hue of the pixel for example. If it is determined that the pixel does not belong to the treatment tool area, the pixel is set as the focus evaluation area as a pixel of the treatment area (S47). If it is determined that the pixel belongs to the treatment tool area, the pixel is not set as the focus evaluation area (S46).

Next, whether or not the process of the steps S41 to S48 has been completed on all of the pixels in the image is determined (S49). If it has not been completed yet, the process returns to the step S41. If it has been completed, the process is terminated.

In the forgoing embodiment, if the pixel belongs to the change area and does not belong to the treatment tool area, the pixel is set as the focus evaluation area as a pixel of the treatment area. Otherwise, the pixel is not set as the focus evaluation area. This configuration makes it possible to exclude the area corresponding to the treatment tool from the area where the local movement of the image exists and determine the resultant area as the treatment area (area where the treatment is being performed on the object). Accordingly, focusing on that pinpoint area is enabled.

Meanwhile, the following process may be performed as a first modified example of the change area determination process in the step S42. That is, in addition to the case that the selected pixel meets requirements of the change area, the selected pixel may be determined to be the change area in the case that a peripheral pixel meets the requirements of change area. That is, even if the selected pixel does not meet the requirements of the change area, the selected pixel may be determined to be a change area if a peripheral (in an area of a predetermined size with the selected pixel as its center, for example) pixel meets the requirements of the change area. This corresponds to expansion of the change area (treatment area) in a spatial direction (expanding an area size in the image).

When operation of the treatment tool is very small, the change area is small, which makes the focus evaluation area small. If the focus evaluation area is too small, direction determination results change frequently, which may make the AF operation unstable. Regarding this point, in this embodiment, since the focus evaluation area is expanded in the spatial direction, the AF operation can be stabilized even if the operation of the treatment tool is very small.

Moreover, the following process may be performed as a second modified example of the change area determination process in the step S42. That is, a pixel determined as the change area in a predetermined number of previous frames may be determined as a change area in the current frame. That is, even if the pixel selected in the current frame does not meet the requirements of the change area, the pixel selected in the current frame may be determined to be the change area if the pixel was determined to belong to the change area in the previous frame. This corresponds to expansion of the change area (treatment area) in a time direction (expanding time in which the pixel is continuously determined as the change area).

If the operation of the treatment tool is faster than a certain speed, a location of the change area in each frame changes drastically, and thus a change of the location of the focus evaluation area between the frames becomes large, which may make the AF operation unstable. For example, assuming that the user performs the treatment with the treatment tool on an area (first area) including the surgical field, then moves the treatment tool quickly to another area (second area) and performs the treatment. If a distance of the first area and a distance of the second area differs significantly, a focus evaluation value of the first area and a focus evaluation value of the second area differs significantly, which may disable an appropriate AF operation. Regarding this point, in this embodiment, since the change area (treatment area) is expanded in the time direction, the change of the location of the focus evaluation area between the frames can be suppressed and the AF operation can be stabilized even if the operation of the treatment tool is fast.

5. Focus Control Section

Figure 8:
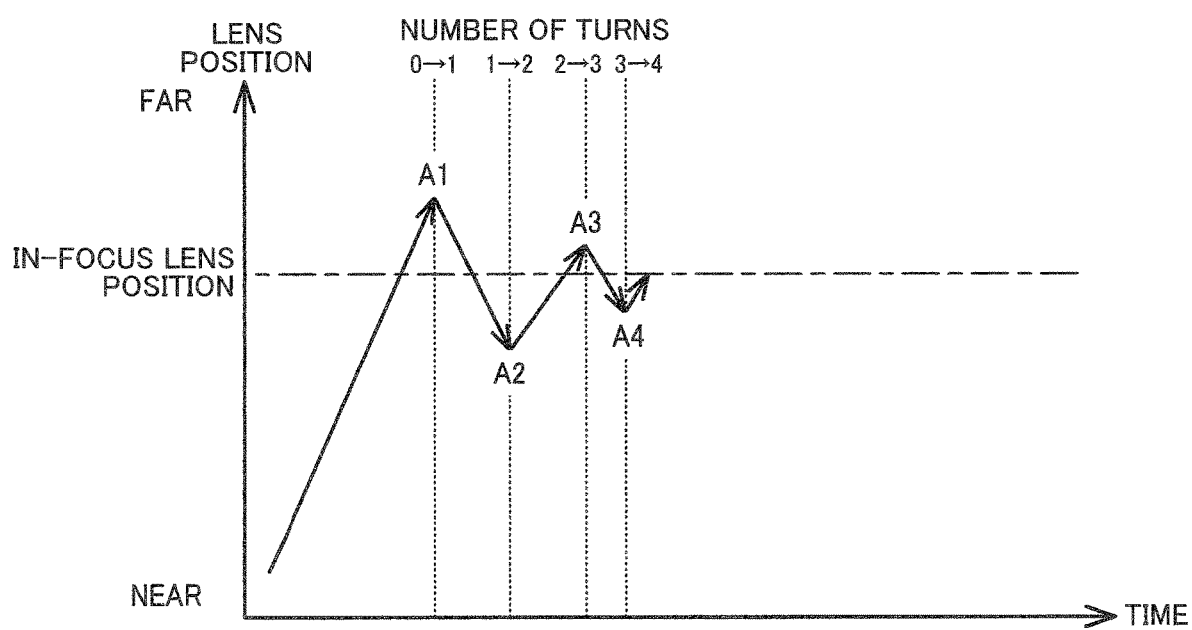
FIG. 8 is a graph illustrating operation of focus control by a wobbling method.

FIG. 8 is a graph illustrating operation of the focus control by a wobbling method. In the wobbling method, a focus lens is moved back and forth with a current focus lens position as a standard, focus evaluation values obtained at front and rear focus lens positions are compared, a moving direction of the focus lens (in-focus direction, direction to get closer to an in-focus lens position) is determined depending on which focus evaluation value is higher, on a NEAR side or a FAR side, and the focus lens is moved in the direction thus determined.

Reference numerals A1, A2, A3 and A4 in FIG. 8 show turns of the moving direction of the focus lens. That is, if polarity of the in-focus direction thus determined is inverted, it is determined to be a turn. In an example shown in FIG. 8, when the AF operation starts, the in-focus direction is determined to be a FAR (far point) direction, and after that, the in-focus direction is repeatedly determined to be the FAR direction several times successively. Then, determination of the in-focus direction changes to a NEAR (near point) direction at a turn A1.

When the in-focus lens position does not change (or moves slowly or slightly), repetition of turns makes the focus lens position closer to the in-focus lens position. The in-focus lens position is a position of the focus lens where the object in the focus evaluation area is in focus. In this embodiment, the number of turns is counted and if the number reaches a predetermined number, the AF operation is stopped (put in a standby state until it is determined that the AF operation is needed next).

FIG. 9 is a flowchart illustrating procedures of a process performed by the focus control section 370. When this process starts, whether or not an in-focus flag is "off" is determined (S61). If the in-focus flag is "on" (that is, already in-focus state), the process is terminated. If the in-focus flag is "off" (that is, focusing is not completed), turn determination is performed (S62 and S63). Note that an initial value of the in-focus flag is "off".

In the turn determination in the steps S62 and S63, whether or not the moving direction of the focus lens, which is determined by the wobbling method, turns in an opposite direction is determined. That is, whether or not the polarity of the in-focus direction is inverted (change from the NEAR direction to the FAR direction, or change from the FAR direction to the NEAR direction) is determined. If the direction does not turn, the process is terminated. If the direction turns, a turn frequency reset determination process (S64 and S65) is performed. Note that an initial value of the number of turns is 0.

In the turn frequency reset determination process in the steps S64 and S65, a lens position at a timing of a previous turn (turn A1 in FIG. 8, for example) and a lens position at a timing of a current turn (turn A2 in FIG. 8, for example) are compared and whether or not a difference absolute value between these positions is higher than a lens position threshold value is determined. If the difference absolute value is higher than the lens position threshold value, it is determined that resetting the number of turns is needed, and if the difference absolute value is equal to or lower than the lens position threshold value, it is determined that resetting the number of turns is not needed. If it is determined that resetting the number of turns is needed in the steps S64 and S65, the number of turns is reset to 0 (S66).

This control makes it possible to redo the AF operation when the object is changed during the AF control. That is, in FIG. 8, if a direction of the camera is changed before completing the AF operation, or if the focus evaluation area (treatment area) is moved, a distance to the object in the focus evaluation area changes, and thus the in-focus lens position moves. For example, if the in-focus lens position moves to the NEAR side between the turns A1 and A2, the lens position at the turn A2 moves to the NEAR side, which makes the difference in the lens position between the turn A1 and the turn A2 larger. In this embodiment, the threshold value determination of the difference in the lens position makes it possible to detect a change in the in-focus lens position and redo the AF operation with respect to the new in-focus lens position.

Meanwhile, in the turn frequency reset determination process in the steps S64 and S65, depending on whether or not the determination result output from the treatment determination section 340 is that the treatment is being performed, the lens position threshold value is changed. That is, the lens position threshold value in the case that the treatment is being performed is set higher than the lens position threshold value in the case that the treatment is not being performed.

When the treatment tool operation (movement of the treatment tool) is large during the treatment, even if the object (direction of camera) is not changed, the treatment area in the image moves, and thus the difference absolute value of the lens position gets larger. In such a case, if the lens position threshold value is low, resetting the number of turns occurs frequently, which may take longer to complete focusing. Therefore, the lens position threshold value is changed to a higher value in the case that the treatment is being performed so as to lower a possibility of determination that resetting the number of turns is needed.

If it is determined that resetting the number of turns is not needed in the steps S64 and S65, the number of turns is incremented (S67). Next, whether or not the number of turns is larger than a turn frequency threshold value is determined (S68). If the number of turns is equal to or smaller than the turn frequency threshold value, the focus lens position at that timing is stored (S71). If the number of turns is larger than the turn frequency threshold value, an in-focus lens position setting process is performed (S69).

In the in-focus lens position setting process in the step S69, an in-focus lens position is calculated based on a focus lens position at that timing (L0) and a stored focus lens position (L1), and the focus lens driving section 220 is driven to move the focus lens to the in-focus lens position. The stored focus lens position (L1) is a lens position stored when the step S71 was executed last time.

In the step S69, depending on whether or not the determination result output from the treatment determination section 340 is that the treatment is being performed, a method for setting the in-focus lens position is changed. That is, if the treatment is not being performed, the in-focus lens position is set in a middle of the position L0 and the position L1. This is because the preset area in the center of the screen needs to be in focus entirely as much as possible when the treatment is not being performed. If the treatment is being performed, the in-focus lens position is set to the position L0. This is because the object of the treatment at the latest timing needs to be in focus at a pinpoint if the treatment is being performed, and thus the position L0 that is the latest focus lens position is set as the in-focus lens position.

When the process ends, the focus control section 370 controls the wobbling operation (one cycle of the wobbling operation to determine the in-focus direction by moving the focus lens back and forth) and starts the process in FIG. 9 again. This process continues until the in-focus flag turns "on".

Although the embodiments to which the present disclosure is applied and the modifications thereof have been described in detail above, the present disclosure is not limited to the embodiments and the modifications thereof, and various modifications and variations may be made without departing from the scope of the present disclosure. The plurality of elements disclosed in the embodiments and the modifications may be combined as appropriate to implement the present disclosure in various ways. For example, some of all the elements described in the embodiments and the modifications may be deleted. Furthermore, elements in different embodiments and modifications may be combined as appropriate. Thus, various modification and application can be made without departing from the gist of the present disclosure. Any term cited with a different term having a broader meaning or the same meaning at least once in the specification and the drawings can be replaced by the different term in any place in the specification and the drawings.

What is claimed is:

1. An autofocus control device comprising:
   a processor configured to implement:
      an image acquisition process of acquiring an object image captured by an imaging section; and
      a treatment determination process of determining whether or not treatment is being performed based on the object image,
   wherein if it is determined that the treatment is not being performed, the processor is configured to implement:
      a focus evaluation area setting process of setting a preset area as a focus evaluation area; and
      a focus control process of calculating a focus evaluation value from the preset area of the object image and performing focus control of the imaging section based on the focus evaluation value calculated from the preset area of the object image, and
   wherein if it is determined that the treatment is being performed, the processor is configured to implement:
      the focus evaluation area setting process of detecting a treatment area where the treatment is being performed on an object based on the object image and setting the treatment area thus detected as the focus evaluation area; and
      the focus control process of calculating the focus evaluation value from the treatment area of the object image and performing the focus control of the imaging section based on the focus evaluation value calculated from the treatment area of the object image.

2. The autofocus control device as defined in claim 1, wherein
   the preset area is an area having a predetermined size and comprising a center of the object image.

3. The autofocus control device as defined in claim 1, wherein,
   in the treatment determination process,
   the processor determines whether or not the treatment is being performed based on a local image change in the object image.

4. The autofocus control device as defined in claim 3, wherein,
   in the treatment determination process,
   the processor determines that the treatment is being performed if an area of where the local image change is determined to exist is within a predetermined range.

5. The autofocus control device as defined in claim 3, wherein,
   in the treatment determination process,
   the processor determines whether or not the local image change exists based on a time change in a pixel value of the object image, or a difference between a motion amount and a peripheral motion amount in a periphery of a position where the motion amount is obtained.

6. The autofocus control device as defined in claim 1, wherein,
   in the focus evaluation area setting process,
   the processor sets the treatment area where the treatment is being performed on an object based on a local image change in the object image.

7. The autofocus control device as defined in claim 6, wherein,
   in the focus evaluation area setting process,
   the processor performs processing for detecting the local image change on the object image, and sets an area where the local image change is detected as the treatment area.

8. The autofocus control device as defined in claim 6, wherein,
   in the focus evaluation area setting process,
   the processor detects the treatment area based on a time change in a pixel value of the object image, or a difference between a motion amount and a peripheral motion amount in a periphery of a position where the motion amount is obtained.

9. The autofocus control device as defined in claim 1, wherein,
   in the focus evaluation area setting process,
   the processor sets an area where the treatment area is expanded as the focus evaluation area, when setting the treatment area as the focus evaluation area.

10. The autofocus control device as defined in claim 9, wherein,
    in the focus evaluation area setting process,
    the processor sets the focus evaluation area to an area where the treatment area is spatially expanded or an area set based on a previous treatment area, as the area where the treatment area is expanded.

11. The autofocus control device as defined in claim 1, wherein,
    in the focus evaluation area setting process,
    the processor
       sets an area where a treatment tool area is eliminated from the preset area as the focus evaluation area, when setting the preset area as the focus evaluation area, and
       sets an area where the treatment tool area is eliminated from the treatment area as the focus evaluation area, when setting the treatment area as the focus evaluation area.

12. The autofocus control device as defined in claim 11, wherein,
    in the focus evaluation area setting process,
    the processor performs a process for detecting a local image change in the object image and a process for detecting the treatment tool area, and sets an area where the treatment tool area is eliminated from an area where the local image change is detected as the focus evaluation area, when setting the treatment area as the focus evaluation area.

13. The autofocus control device as defined in claim 1, wherein,
    in the focus control process,
    the processor changes a control parameter for the focus control according to the determination result of the treatment determination process.

14. The autofocus control device as defined in claim 13, wherein,
    in the focus control process,
    the processor performs a focus completion determination for determining whether or not autofocus operation is completed, and if the autofocus operation is determined to be completed, the processor stops the autofocus operation and changes the control parameter of the focus completion determination according to the determination result of the treatment determination process.

15. The autofocus control device as defined in claim 1, wherein,
    an area of the treatment area is smaller than an area of the preset area.

16. An endoscope apparatus comprising the autofocus control device as defined in claim 1.

17. An operation method of an autofocus control device, the operation method comprising:

acquiring an object image captured by an imaging section;

determining whether or not treatment is being performed based on the object image captured by the imaging section;

if it is determined that the treatment is not being performed:
 setting a preset area as a focus evaluation area; and
 calculating a focus evaluation value from the preset area of the object image and performing focus control of the imaging section based on the focus evaluation value calculated from the preset area of the object image; and if it is determined that the treatment is being performed:
 detecting a treatment area where the treatment is being performed on an object based on the object image and setting the treatment area thus detected as the focus evaluation area; and
 calculating the focus evaluation value from the treatment area of the object image and performing the focus control of the imaging section based on the focus evaluation value calculated from the treatment area of the object image.

\* \* \* \* \*